(12) United States Patent
Sakaguchi

(10) Patent No.: US 7,867,449 B2
(45) Date of Patent: Jan. 11, 2011

(54) PIPETTE TIP, LIQUID RECEIVING STRUCTURE, LIQUID SUPPLY DEVICE

(75) Inventor: Yasunobu Sakaguchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 697 days.

(21) Appl. No.: 11/723,231

(22) Filed: Mar. 19, 2007

(65) Prior Publication Data
US 2007/0231214 A1 Oct. 4, 2007

(30) Foreign Application Priority Data
Mar. 28, 2006 (JP) ............................. 2006-088378

(51) Int. Cl.
*B01L 3/02* (2006.01)
(52) U.S. Cl. .................... 422/100; 73/863.32; 73/864; 73/864.01
(58) Field of Classification Search ................ 422/100; 73/863.32, 864, 864.1
See application file for complete search history.

(56) References Cited

U.S. PATENT DOCUMENTS

| | | | | |
|---|---|---|---|---|
| 3,713,775 A | * | 1/1973 | Schmitz ........................ 422/72 |
| 5,223,225 A | * | 6/1993 | Gautsch ........................ 422/100 |
| 5,807,524 A | * | 9/1998 | Kelly et al. .................. 422/100 |
| 6,422,248 B1 | * | 7/2002 | Furst et al. ................ 134/22.11 |
| 6,566,145 B2 | * | 5/2003 | Brewer ........................ 436/178 |
| 6,967,004 B2 | * | 11/2005 | Rainin et al. ................. 422/100 |
| 7,081,228 B1 | * | 7/2006 | Ito .............................. 422/100 |
| 7,311,882 B1 | * | 12/2007 | Renzi .......................... 422/103 |
| 7,335,337 B1 | * | 2/2008 | Smith .......................... 422/100 |
| 7,374,724 B2 | * | 5/2008 | Ingenhoven et al. ......... 422/101 |
| 7,579,026 B2 | * | 8/2009 | Myhill et al. ................ 424/729 |
| 2005/0175511 A1 | * | 8/2005 | Cote et al. ................... 422/100 |
| 2006/0257290 A1 | * | 11/2006 | Shimizu ....................... 422/100 |
| 2007/0231215 A1 | * | 10/2007 | Mototsu ....................... 422/100 |

FOREIGN PATENT DOCUMENTS

JP 2006-64514 A 3/2006

* cited by examiner

*Primary Examiner*—Brian R Gordon
(74) *Attorney, Agent, or Firm*—Sughrue Mion, PLLC

(57) ABSTRACT

A pipette tip includes a cylindrical distal end portion in which an opening that dispenses or draws in liquid is formed and a body portion that has a cylindrical shape whose outer periphery has a larger diameter than that of the distal end portion and which configures an outer peripheral step portion between itself and the distal end portion.

6 Claims, 11 Drawing Sheets

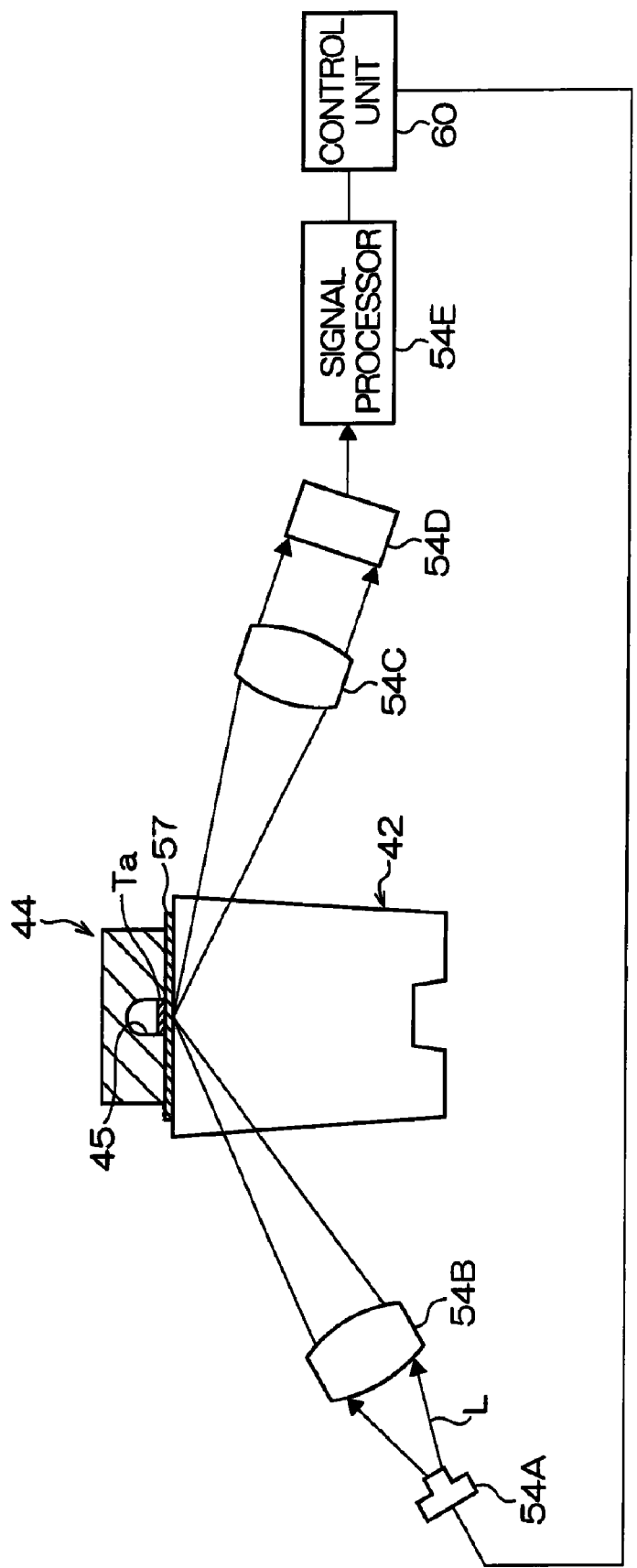

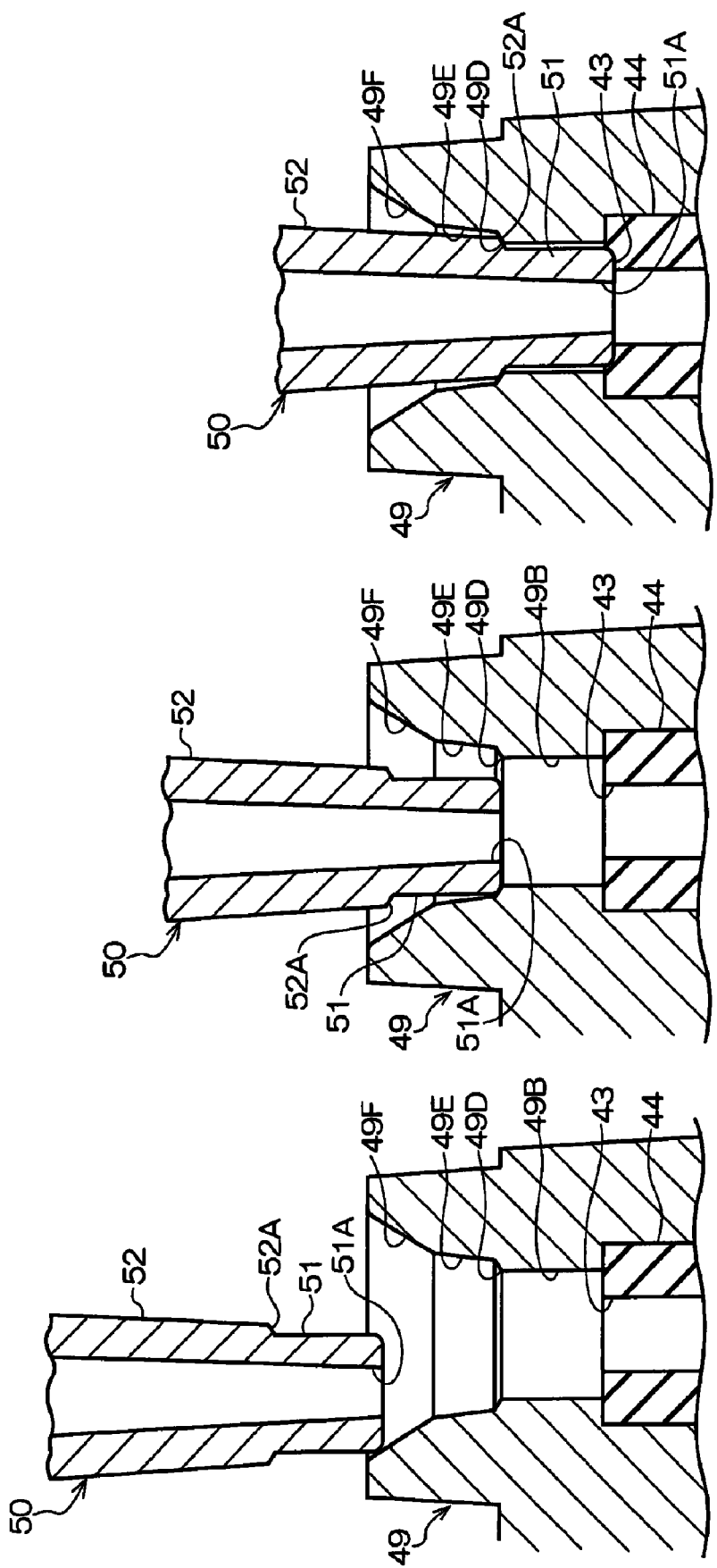

PIPETTE TIP, LIQUID RECEIVING STRUCTURE, LIQUID SUPPLY DEVICE

CROSS-REFERENCE TO RELATED APPLICATIONS

This application claims priority under 35 USC 119 from Japanese Patent Applications No. 2006-088378, the disclosure of which is incorporated by reference herein.

BACKGROUND OF THE INVENTION

1. Field of the Invention

The present invention relates to a pipette tip that dispenses and draws in liquid, a liquid receiving structure into which liquid enters and from which liquid exits using the pipette tip, and a liquid supply device disposed with the pipette tip and the liquid receiving structure.

2. Description of the Related Art

Conventionally, liquids have been supplied and drawn in using a pipette tip. For example, Japanese Patent Application Laid-Open (JP-A) No. 2006-064514 discloses an assay device where, when a reagent including a sensing substance is to be supplied to a flow path in which a device under test is fixed, the distal ends of pipette tips are inserted into an inlet and outlet of the flow path, the reagent is dispensed from the pipette tip in the inlet, and buffer liquid inside the flow path is drawn in by the pipette tip in the outlet.

When the distal ends of pipette tips are repeatedly inserted and pulled out when the leading ends of the pipette tips are inserted into a flow path to supply liquid as in Japanese Patent Application Laid-Open (JP-A) No. 2006-064514, sometimes the distal ends of the pipette tips and the vicinities of the insertion openings in the flow path become deformed due to degradation.

Further, sometimes the height of the liquid surface after the pipette tips have been removed becomes unstable because the flow path becomes pushed wider and the injection amount becomes unstable due to insertion of the distal end portions of the pipette tips into the flow path.

Moreover, when the pipette tips that have been inserted into the flow path are to be pulled out, sometimes the pipette tips attached to liquid supply nozzles come off of the nozzles and remain inserted in the flow path due to pullout resistance.

SUMMARY OF THE INVENTION

The present invention has been made in view of the above circumstances, and it is an object thereof to provide a pipette tip that is difficult to degrade and is capable of appropriately supplying liquid to a flow path, a liquid receiving structure that receives liquid supplied thereto by the pipette tip, and a liquid supply device disposed with the pipette tip and the liquid receiving structure.

In order to address this problem, a pipette tip of a first aspect of the invention comprises: a cylindrical distal end portion in which an opening that dispenses or draws in liquid is formed; and a body portion that has a cylindrical shape whose outer periphery has a larger diameter than that of the distal end portion and which configures an outer peripheral step portion between itself and the distal portion.

In the pipette tip of the present invention, the outer peripheral step portion whose body portion side has a large diameter is formed on the outer periphery between the distal end portion and the body portion. By performing positioning between the pipette tip and the opening in a flow path using the outer peripheral step portion, liquid can be supplied to the flow path without having to insert the distal end portion of the pipette tip into the flow path.

Consequently, degradation of the distal end portion of the pipette tip resulting from inserting and pulling out the pipette tip is controlled. Further, because the pipette tip is not inserted into the flow path, the injection amount can be stabilized without the flow path being pushed apart, and the height of the liquid surface after the pipette tip has been pulled out can be made constant.

The outer peripheral step portion has a tapered shape, and the distal end portion side thereof has a small diameter.

According to this configuration, even if the outer peripheral portion of the pipette tip inserted toward the flow path from the distal end portion impacts another member, the pipette tip can be smoothly inserted because there is inclination in the insertion direction.

A liquid receiving structure of a second aspect of the invention is a liquid receiving structure into which liquid enters and from which liquid exits using a pipette tip including a cylindrical distal end portion in which an opening that dispenses or draws in liquid is formed and a body portion that has a cylindrical shape whose outer periphery has a larger diameter than that of the distal end portion and which configures an outer peripheral step portion between itself and the distal end portion, the liquid receiving structure comprising: a flow path member having formed therein an exit/entry opening through which the liquid enters and from which the liquid exits and which configures a flow path communicated with the exit/entry opening; and a receiving member that is disposed on the outside of the flow path member and in which a recessed portion continuous with the exit/entry opening is configured, wherein the recessed portion is configured by a first inner wall portion that is disposed at the flow path member side, has a shape along the distal end portion of the pipette tip, and whose length in an insertion direction of the pipette tip is shorter than the length of the distal end portion in the insertion direction of the pipette tip, and a second inner wall portion whose inner diameter is larger than that of the first inner wall portion and which configures an inner peripheral step portion between itself and the first inner wall portion, and a distal end surface of the pipette tip is pushed against an end surface of the flow path member in which the exit/entry opening is formed, whereby an opening in the pipette tip and the exit/entry opening of the flow path member are communicated and one of the distal end surface of the pipette tip and the end surface of the flow path member becomes deformed such that the outer peripheral step portion is brought into contact with the inner peripheral step portion.

The liquid receiving structure of the present invention includes the flow path member and the receiving member. The flow path member includes the exit/entry opening through which the liquid is supplied and from which the liquid is discharged. The receiving member is disposed on the outside of the flow path member, and a recessed portion that communicates with the exit/entry opening of the flow path member is configured therein.

The inside of the recessed portion is configured by the first inner wall portion and the second inner wall portion. Because the length of the first inner wall portion in the insertion direction of the pipette tip is shorter than the length of the distal end portion in the insertion direction of the pipette tip, the outer peripheral step portion of the pipette tip and the inner peripheral step portion of the receiving member do not come into contact with each other simply when the distal end surface of the pipette tip is brought into contact with the end surface of the exit/entry opening of the flow path member. The distal end surface of the pipette tip is pushed against the end surface, whereby one of the distal end surface of the pipette tip and the end surface of the flow path member becomes deformed and the inner peripheral step portion and the outer peripheral step portion are brought into contact with each other. Thus, the opening in the pipette tip and the exit/entry opening in the flow path member become communicated, positioning in the insertion direction is also performed, and in this state the liquid can be dispensed and drawn in by the pipette tip.

According to this liquid receiving structure, the liquid can be supplied to the flow path without having to insert the distal end of the pipette tip into the flow path. Consequently, degradation of the distal end portion of the pipette tip and of the vicinity of the exit/entry opening in the flow path member resulting from inserting and pulling out the pipette tip is controlled. Further, because the pipette tip is not inserted into the flow path, the injection amount can be stabilized without the flow path being pushed apart, and the height of the liquid surface after the pipette tip has been pulled out can be made constant.

In the liquid receiving structure of the present invention, the outer peripheral step portion has a tapered shape, and the distal end portion side thereof has a small diameter, and the inner peripheral step portion of the receiving member may have a tapered shape along the outer peripheral step portion.

According to this configuration, even if the outer peripheral portion of the pipette tip inserted toward the flow path from the distal end portion impacts the inner peripheral step portion of the liquid receiving member, the pipette tip can be smoothly inserted toward the flow path member side of the recessed portion because there is inclination in the insertion direction.

Further, in the liquid receiving structure of the present invention, the flow path member may be softer than the pipette tip.

By configuring the flow path member to be softer than the pipette tip, the flow path member can be deformed by the distal end surface of the pipette tip.

Further, in the liquid receiving structure of the present invention, the flow path member may be configured by a soft material that is elastically deformable when the pipette tip is pushed against the flow path member.

By configuring the flow path member with a soft material, the flow path member can be easily deformed when the distal end surface of the pipette tip is pushed against it.

A liquid supply device of a third aspect of the present invention comprises: a pipette tip including a cylindrical distal end portion in which an opening that dispenses or draws in liquid is formed and a body portion that has a cylindrical shape whose outer periphery has a larger diameter than that of the distal end portion and which configures an outer peripheral step portion between itself and the distal end portion; a flow path member having formed therein an exit/entry opening through which the liquid enters and from which the liquid exits and which configures a flow path communicated with the exit/entry opening; and a receiving member that is disposed on the outside of the flow path member and in which a recessed portion continuous with the exit/entry opening is configured, wherein the recessed portion is configured by a first inner wall portion that has a shape along the distal end portion of the pipette tip and whose length in an insertion direction of the pipette tip is shorter than the length of the distal end portion in the insertion direction of the pipette tip, and a second inner wall portion whose inner diameter is larger than that of the first inner wall portion and which configures an inner peripheral step portion between itself and the first inner wall portion, and a distal end surface of the pipette tip is pushed against an end surface of the flow path member in which the exit/entry opening is formed, whereby one of the distal end surface of the pipette tip and the end surface of the flow path member becomes deformed such that the outer peripheral step portion is brought into contact with the inner peripheral step portion.

Because the liquid supply device of the present invention includes the pipette tip of the first aspect and the liquid receiving structure of the second aspect, it can supply liquid to a flow path with a pipette tip without having to insert the pipette tip into the flow path. Consequently, degradation of the distal end portion of the pipette tip and of the vicinity of the exit/entry opening in the flow path member resulting from inserting and pulling out the pipette tip is controlled. Further, because the pipette tip is not inserted into the flow path, the injection amount can be stabilized without the flow path being pushed apart, and the height of the liquid surface after the pipette tip has been pulled out can be made constant.

BRIEF DESCRIPTION OF THE DRAWINGS

An exemplary embodiment of the present invention will be described in detail based on the following figures, wherein:

FIG. 9 is a general view of the vicinity of an optical assay unit of the biosensor pertaining to the exemplary embodiment of the invention;

FIGS. 11A to 11C are views showing an example of a process where a pipette tip is inserted into a receiving portion pertaining to the exemplary embodiment of the invention.

DETAILED DESCRIPTION OF THE INVENTION

An exemplary embodiment of the present invention will be described below with reference to the drawings.

A liquid supply device of the present invention is applied to a biosensor 10. The biosensor 10 is a surface plasmon sensor that utilizes surface plasmon resonance occurring in the surface of a metal film to assay the interaction between a ligand D and an analyte A.

Figure 1:
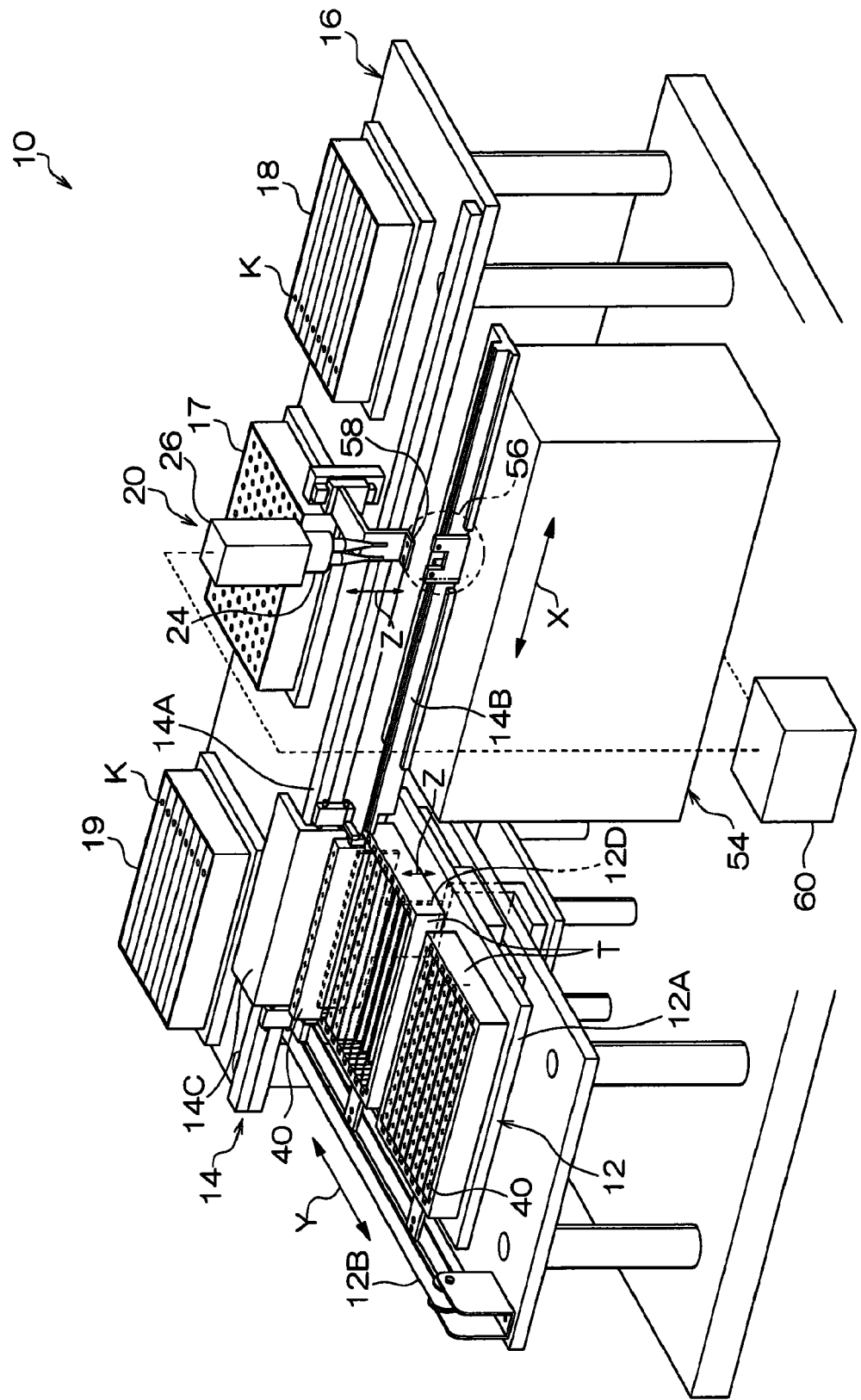
FIG. 1 is a total perspective view of a biosensor pertaining to the exemplary embodiment of the invention.

As shown in FIG. 1, the biosensor 10 is disposed with a tray holding unit 12, a conveyance unit 14, a container platform 16, a liquid drawing/dispensing unit 20, an optical assay unit 54, and a control unit 60.

The tray holding unit 12 is configured to include a platform 12A and a belt 12B. The platform 12A is attached to the belt 12B, which is disposed in the direction of arrow Y, and is configured to be movable in the direction of arrow Y by the rotation of the belt 12B. Trays T are placed on the platform 12A. Sensor sticks 40 are housed in the trays T. The sensor sticks 40 are chips in which the ligands D are fixed, and the details thereof will be described later. A pushup mechanism 12D that pushes up the sensor sticks 40 as far as the position of a later-described stick holding member 14C is disposed below the platform 12A.

Figure 2:
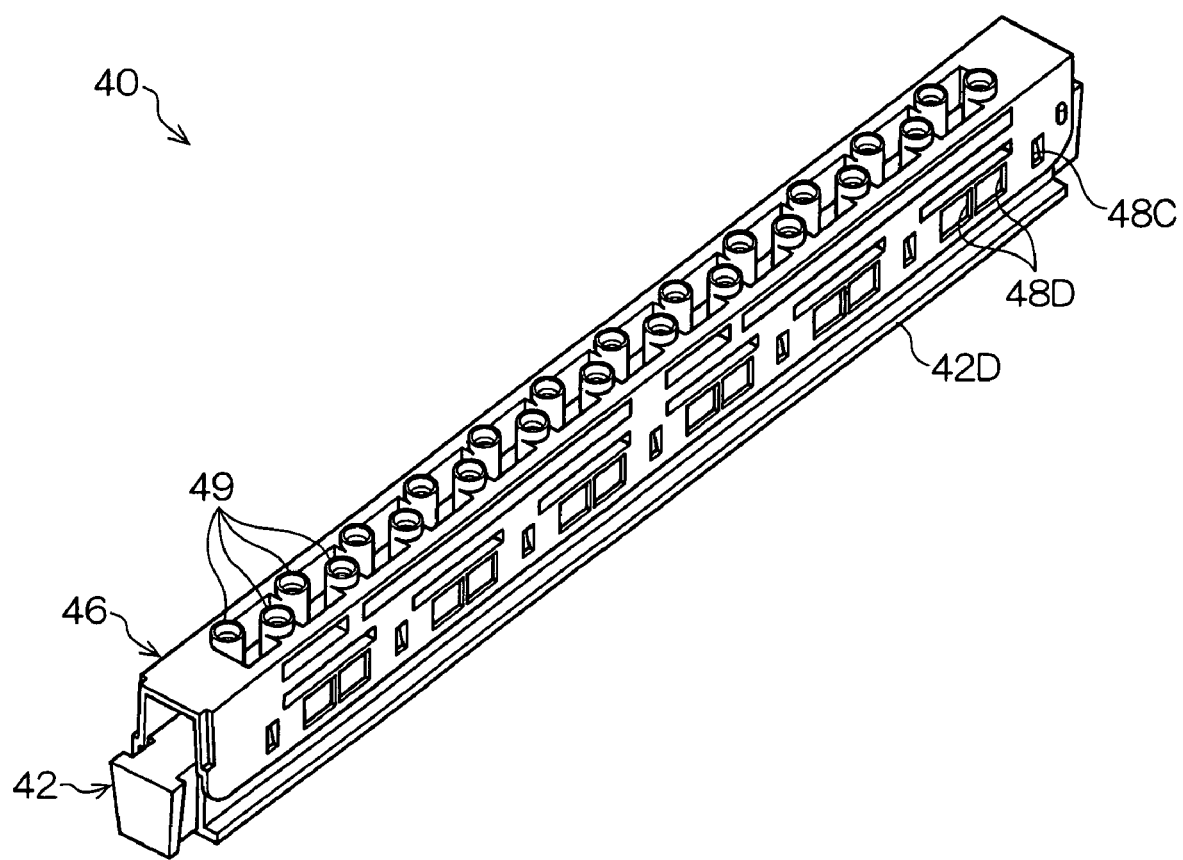
FIG. 2 is a perspective view of a sensor stick pertaining to the exemplary embodiment of the invention.
Figure 3:
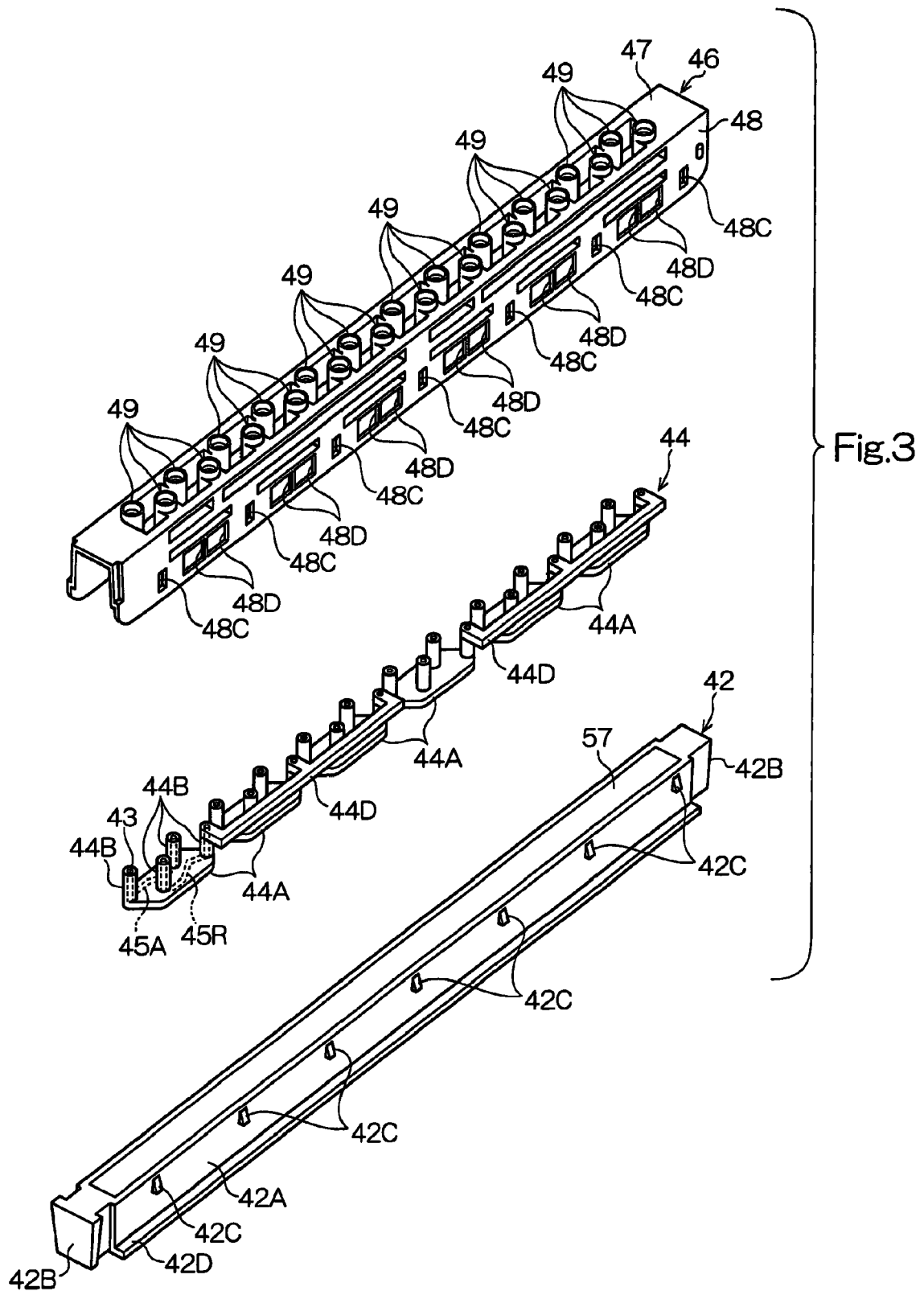
FIG. 3 is an exploded perspective view of the sensor stick pertaining to the exemplary embodiment of the invention.

As shown in FIG. 2 and FIG. 3, each of the sensor sticks 40 is configured by a dielectric block 42, a flow path member 44, and a holding member 46.

The dielectric block 42 is configured by transparent resin or the like that is transparent to light beams and is disposed with a prism portion 42A whose cross section is shaped like a trapezoidal rod and held portions 42B that are formed on both end portions of the prism portion 42A integrally with the prism portion 42A. A metal film 57 is formed on the upper surface of the wider of two mutually parallel surfaces of the prism portion 42A. The dielectric block 42 functions as a prism such that, during assay by the biosensor 10, light beams are made incident from one of two side surfaces of the prism portion 42A that face each other but are not mutually parallel, and light beams totally reflected by the boundary with the metal film 57 are emitted from the other side.

Figure 4:
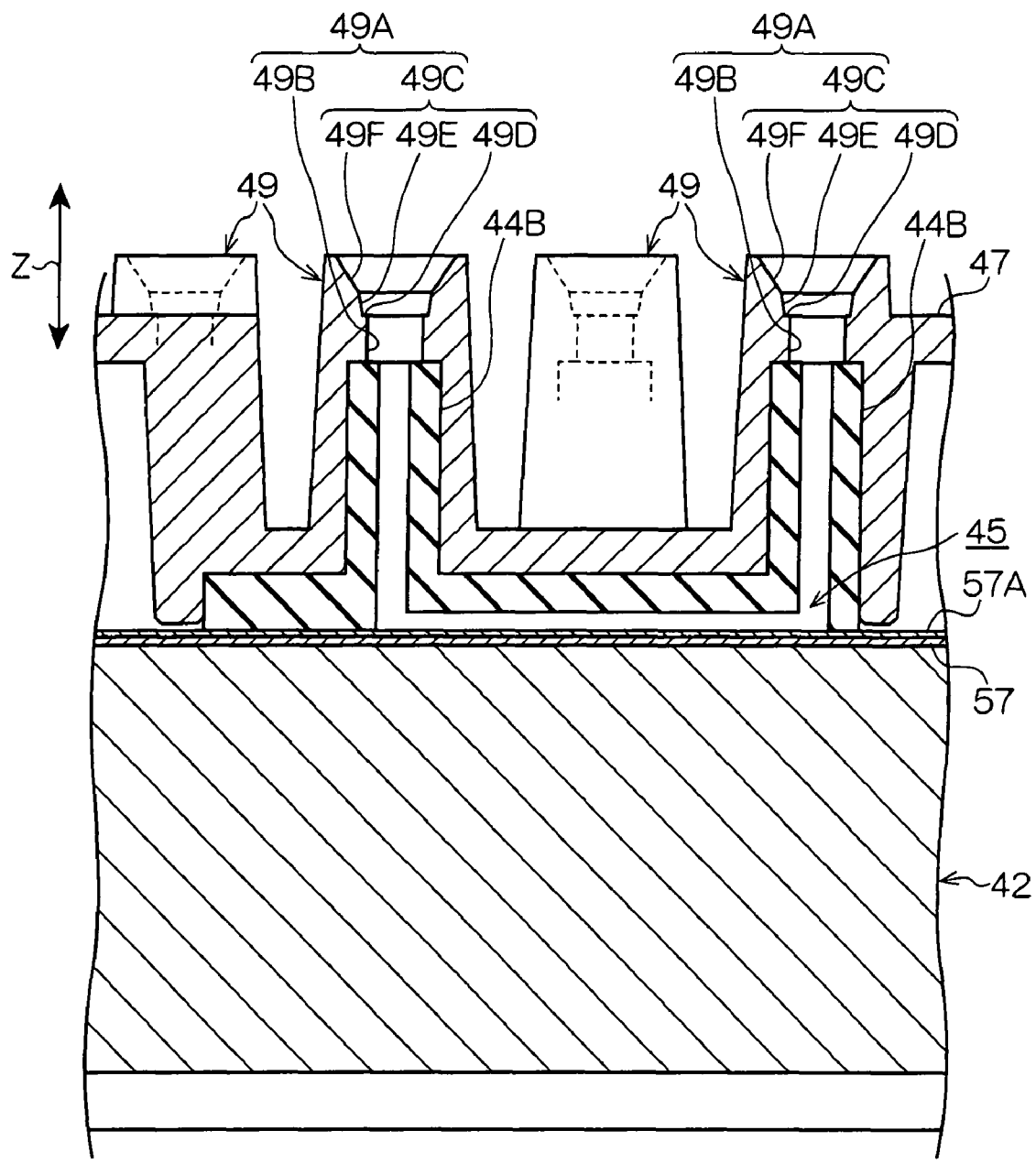
FIG. 4 is a cross-sectional view of one liquid flow path portion of the sensor stick pertaining to the exemplary embodiment of the invention.

As shown in FIG. 4, a linker layer 57A is formed on the surface of the metal film 57. The linker layer 57A is a layer for fixing proteins Ta onto the metal film 57.

Engagement projections 42C that engage with the holding member 46 are formed on both side surfaces of the prism portion 42A along their upper end edges. Further, a flange portion 42D that engages with an unillustrated rail for conveyance is formed on the underside of the prism portion 42A along its side end edges.

As shown in FIG. 3, the flow path member 44 is disposed with six base portions 44A, and four circular cylinder members 44B are erectly disposed on each of the base portions 44A. The upper portion of one of the erectly disposed circular cylinder members 44B on each of the base portions 44A is coupled by a coupling member 44D for every three of the base portions 44A. The flow path member 44 is configured by a soft, elastically deformable material such as an amorphous polyolefin elastomer.

Figure 5:
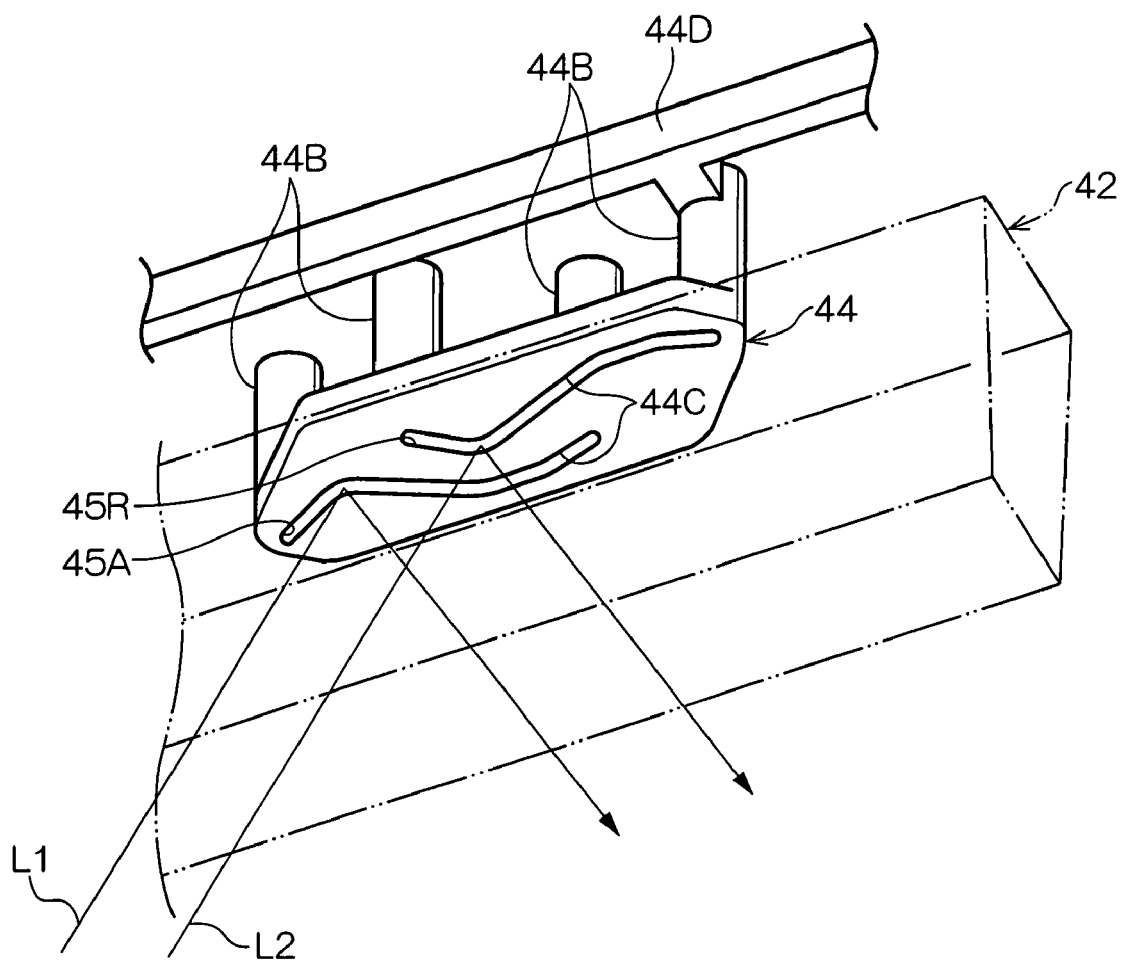
FIG. 5 is a view showing a state where light beams are made incident on the sensor stick pertaining to the exemplary embodiment of the invention.
Figure 6:
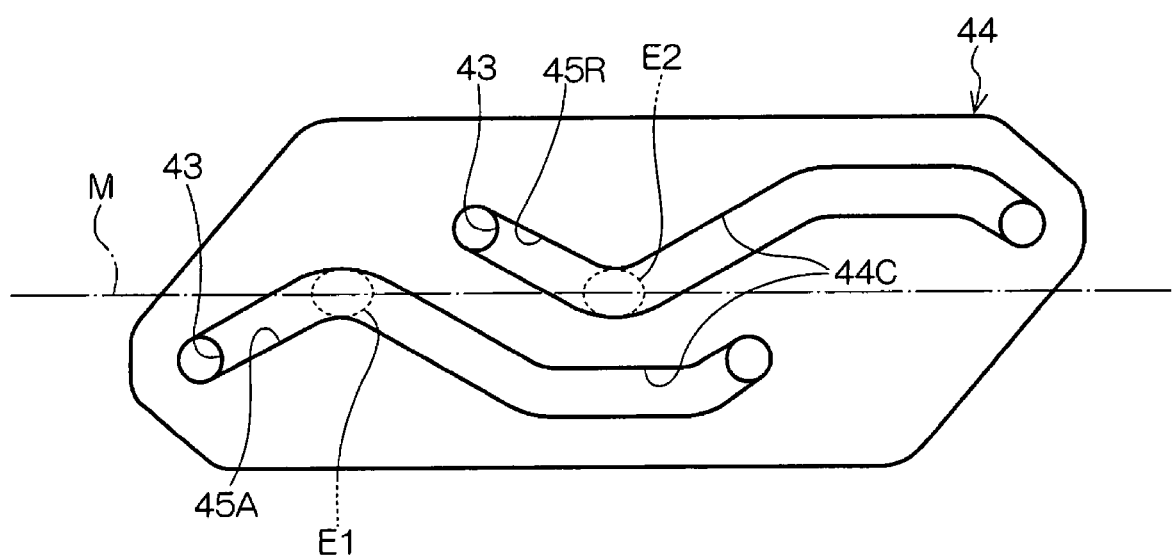
FIG. 6 is a bottom view of one flow path member pertaining to the exemplary embodiment of the invention.

As shown in FIG. 5 and FIG. 6, two generally S-shaped flow path grooves 44C are formed in the bottom surface of each of the base portions 44A. End portions of each of the flow path grooves 44C are communicated with a hollow portion in one of the circular cylinder members 44B. The bottom surface of each of the base portions 44A is tightly adhered to the upper surface of the dielectric block 42, and liquid flow paths 45 are configured by the hollow portions and by spaces configured between the flow path grooves 44C and the upper surface of the dielectric block 42. Two liquid flow paths 45 are configured in one base portion 44A. In each of the liquid flow paths 45, an exit/entry opening 43 of the liquid flow path 45 is configured in the upper end surface of each of the circular cylinder members 44B.

Here, of the two liquid flow paths 45, one is used as an assay flow path 45A and the other is used as a reference flow path 45R. Assay is performed in a state where the proteins Ta are fixed onto the metal film 57 of the assay flow path 45A and where the proteins Ta are not fixed onto the metal film 57 of the reference flow path 45R. As shown in FIG. 5, light beams L1 and L2 are made incident respectively at the assay flow path 45A and the reference flow path 45R. As shown in FIG. 6, curved portions of the S shapes disposed on a midline M of the base portion 44A are irradiated by the light beams L1 and L2. Below, the region of the flow path 45A irradiated by the light beam L1 will be called an "assay region E1" and the region of the flow path 45R irradiated by the light beam L2 will be called a "reference region E2". The reference region E2 is a region where assay for correcting data obtained from the assay region E1 where the proteins Ta are fixed is performed.

The holding member 46 has an elongate shape and includes an upper surface member 47 and two side surface plates 48 that are configured like a lid. Engagement holes 48C that engage with the engagement projections 42C of the dielectric block 42 are formed in the side surface plates 48, and windows 48D are formed in portions of the side surface plates 48 that correspond to the light paths of the light beams L1 and L2. The holding member 46 is attached to the dielectric block 42 as a result of the engagement holes 46C and the engagement projections 42C engaging with each other. It will be noted that, as described later, the flow path member 44 is molded integrally with the holding member 46 and is disposed between the holding member 46 and the dielectric block 42.

Receiving portions 49 are formed in the upper surface member 47 at positions corresponding to the circular cylinder members 44B of the flow path member 44. As shown in FIG. 4, each of the receiving portions 49 has a substantially circular cylinder-like shape, and the circular cylinder members 44B are disposed in hollow lower portions of the receiving portions 49. Further, a recessed portion 49A that communicates with the exit/entry opening 43 is configured further toward the upper side of each of the receiving portions 49 than the hollow circular cylinder members 44B. Pipette tips 50 are inserted into the recessed portions 49A.

The holding member 46 is configured by a material that is harder than that of the flow path member 44, such as a crystalline polyolefin.

Figure 7:
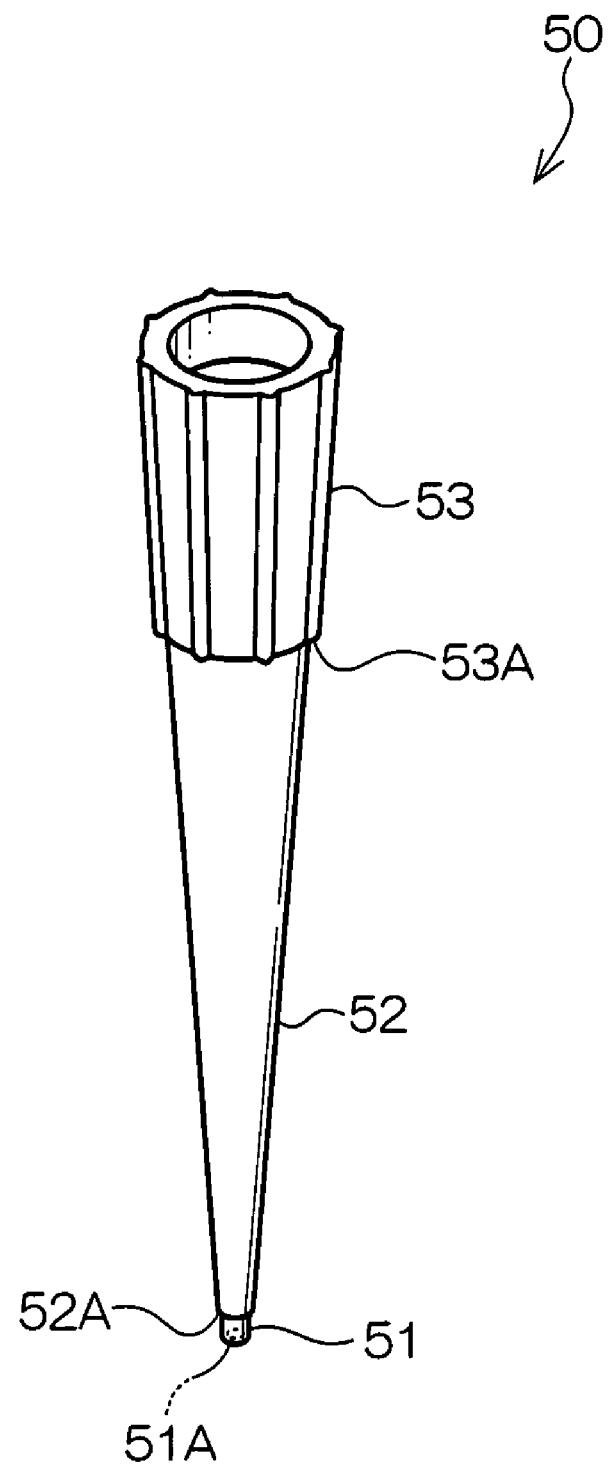
FIG. 7 is a perspective view of a pipette tip pertaining to the exemplary embodiment of the invention.

As shown in FIG. 7, each of the pipette tips 50 has a substantially conical cylinder-like shape and is configured by a distal end portion 51, a body portion 52, and a holding portion 53. The distal end portion 51 has a circular cylinder-like shape, and an opening 51A that dispenses or draws in liquid is configured in the most distal end of the distal end portion 51 in the insertion direction. The body portion 52 has a conical cylinder-like shape whose outer periphery is larger than that of the distal end portion 51, and an outer peripheral step portion 52A is configured between the body portion 52 and the distal end portion 51. The outer peripheral step portion 52A is configured in a tapered shape whose distal end portion 51 side has a small diameter. The outer periphery of the holding portion 53 has a larger diameter than that of the body portion 52, and a holding step portion 53A is configured between the holding portion 53 and the body portion 52. The holding step portion 53A is a portion that is used when holding the pipette tip 50 in a pipette tip stocker including an upper surface plate in which an unillustrated holding hole is configured.

As shown in FIG. 4, the recessed portion 49A of each of the receiving portions 49 is configured so as to be surrounded by a first inner wall portion 49B at the flow path member 44 side and a second inner wall portion 49C. The first inner wall portion 49B has a shape along the distal end portion 51 where its length along an insertion direction Z of the pipette tip 50 is slightly shorter than that of the distal end portion 51 of the pipette tip 50 and has a slightly larger diameter than the outer diameter of the distal end portion 51.

The second inner wall portion 49C is configured by an inner peripheral step portion 49D between the first inner wall portion 49B and the second inner wall portion 49C, a central inner wall portion 49E adjacent to the inner peripheral step portion 49D, and an uppermost upper wall portion 49F. The inner peripheral step portion 49D is continuous from the first inner wall portion 49B and is configured in a tapered shape whose upper portion has a large diameter along the outer peripheral step portion 52A of the pipette tip 50. The central inner wall portion 49E is continuous with the inner peripheral step portion 49D and is configured in a tapered shape whose portion above the pipette tip 50 has a large diameter. The upper inner wall portion 49F is continuous with the central inner wall portion 49E and is configured in a tapered shape whose portion above the pipette tip 50 has an even larger diameter.

The holding member 46 and the flow path member 44 are integrally molded by two-color molding (double molding) where different materials are combined together and molded inside the same mold.

As shown in FIG. 1, the conveyance unit 14 of the biosensor 10 is configured to include an upper guide rail 14A, a lower guide rail 14B, and a stick holding member 14C. The upper guide rail 14A and the lower guide rail 14B are disposed above the tray holding unit 12 and the optical assay unit 54 and horizontally in the direction of arrow X, which is orthogonal to the direction of arrow Y. The stick holding member 14C is attached to the upper guide rail 14A. The stick holding member 14C is configured such that it is capable of holding the held portions 42B on both end portions of each of the sensor sticks 40 and is movable along the upper guide rail 14A. The lower guide rail 14B engages with the flange portion 42D in the sensor stick 40 held in the stick holding member 14C, and the stick holding member 14C moves in the direction of arrow X, whereby the sensor stick 40 is conveyed to an assay unit 56 on the optical assay unit 54. Further, the assay unit 56 is disposed with a holding member 58 that holds the sensor stick 40 during assay. The holding member 58 is configured to be movable in the Z direction by an unillustrated drive mechanism and pushes from above the sensor stick 40 disposed in the assay unit 56.

An analyte solution plate 17, a buffer liquid stocker container 18, and a waste liquid container 19 are placed on the container platform 16. The analyte solution plate 17 is partitioned into a matrix and stocked with various kinds of analyte solutions. The buffer liquid stocker container 18 is configured by plural containers and stocked with plural kinds of buffer liquids having different refractive indexes. Openings K into which the later-described pipette tips 50 are insertable are formed in the buffer liquid stocker container 18. The waste liquid container 19 is configured by plural containers and, similar to the buffer liquid stocker container, openings K into which the pipette tips 50 are insertable are formed therein.

As shown in FIG. 1, the liquid drawing/dispensing unit 20 is configured to include a head 24 and a drawing/dispensing drive unit 26. The head 24 is configured to be movable in the direction of arrow Y (see FIG. 1) along an unillustrated conveyance rail. Further, the head 24 is configured to be movable also in the vertical direction (the direction of arrow Z) by an unillustrated drive mechanism inside the head 24.

Figure 8:
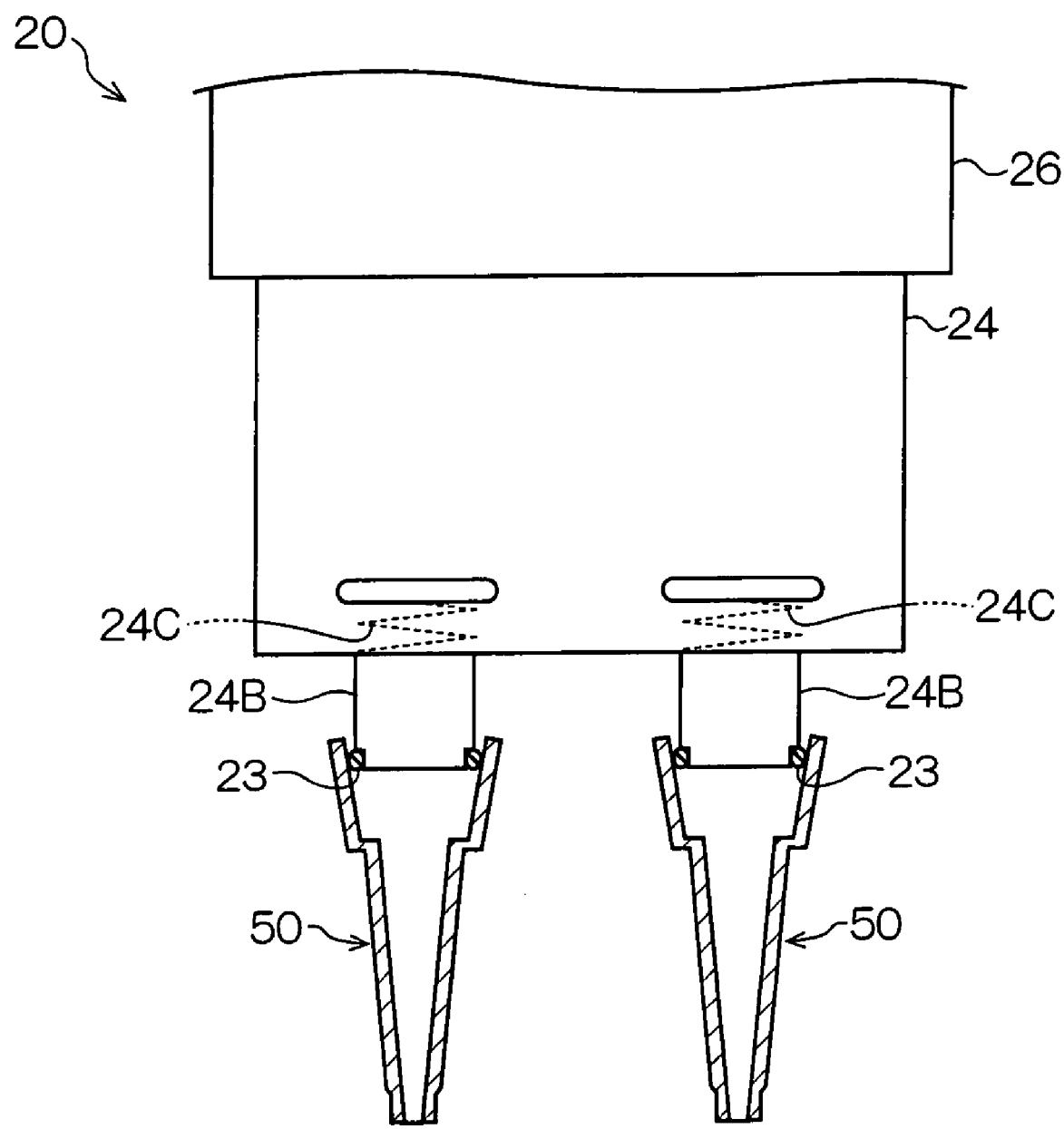
FIG. 8 is a general configural view of a liquid drawing/dispensing unit pertaining to the exemplary embodiment of the invention.

As shown in FIG. 8, the head 24 is disposed with a pair of 24B. The pipette tips 50 are attached to the nozzles 24B via elastic links 23. The elastic links here include, but are not limited to, O-rings, and may be any links as long as they have elasticity and include the function of contacting and sealing the nozzles and the pipette tips.

The drawing/dispensing drive unit 26 is disposed with an unillustrated pump and causes liquid to be dispensed from the pipette tips 50 and liquid to be drawn into the pipette tips 50 by pressurization or depressurization. Springs 24C that receive force from the pipette tips 50 are attached to the nozzles 24B.

As shown in FIG. 9, the optical assay unit 54 is configured to include a light source 54A, a first optical system 54B, a second optical system 54C, a light receiver 54D, and a signal processor 54E. A diffuse light beam L is emitted from the light source 54A. The light beam L becomes two light beams L1 and L2 via the first optical system 54B, and the light beams L1 and L2 are respectively made incident at the assay region E1 and the reference region E2 of the dielectric block 42 disposed in the assay unit 56. In the assay region E1 and the reference region E2, the light beams L1 and L2 include various incident angle components with respect to the boundary between the metal film 57 and the dielectric block 42 and are made incident at an angle equal to or greater than the total reflection angle. The light beams L1 and L2 are totally reflected at the boundary between the dielectric block 42 and the metal film 57. The totally reflected light beams L1 and L2 are also reflected with various reflection angle components. The totally reflected light beams L1 and L2 are received by the light receiver 54D via the second optical system 54C, each of the light beams L1 and L2 is photoelectrically converted, and light detection signals are outputted to the signal processor 54E. In the signal processor 54E, predetermined processing is performed on the basis of the inputted light detection signals, and data of total reflection angles of the assay region E1 and the reference region E2 (called "total reflection angle data" below) are determined. The total reflection angle data are outputted to the control unit 60.

Next, assay by the biosensor 10 will be described. Assay is performed by supplying an analyte solution YA to the sensor stick 40 where the proteins Ta are fixed in the assay flow path 45A and detecting signal changes in the assay region E1 at that time.

When the sensor stick 40 is conveyed to and disposed in the assay unit 56, the assay region E1 and the reference region E2 are irradiated respectively with the light beams L1 and L2. The light beams L1 and L2 are totally reflected by the assay region E1 and the reference region E2, diffused, and emitted to the outside through the prism surface of the dielectric block 42. The light beams L1 and L2 emitted to the outside are received by the light receiver 54D via the second optical system 54C, each of the light beams L1 and L2 is photoelectrically converted, and light detection signals are outputted to the signal processor 54E. In the signal processor 54E, predetermined processing is performed on the basis of the inputted light detection signals, the total reflection angle data of the assay region E1 and the reference region E2 are determined, and the total reflection angle data are outputted to the control unit 60.

Here, the total reflection angle data in the assay region E1 when liquid not reacting with the proteins Ta flows in the liquid flow paths 45 and the total reflection angle data in the reference region E2 become substantially equivalent. The angle difference equal to the change in the total reflection angle data of the reference region E2 subtracted from the change in the total reflection angle data of the assay region E1 when the analyte solution YA flows in the liquid flow path 45 corresponds to the bonding amount between the proteins Ta of the assay region E1 and the analyte A of the analyte solution YA.

The total reflection angle data are continuously outputted to the control unit 60 from the signal processor 54E, and in the control unit 60, assay data representing the bonding amount are calculated are stored on the basis of the total reflection angle data.

The value of the assay data represents the bonding amount per unit area between the proteins Ta of the assay region E1 and the analyte A, and the unit of the value of the assay data is RU (resonance units). In relation to the acquisition of assay data representing the bonding amount, one can refer to *Seitai busshitsu sayō no riaru taimu kaiseki jikkenhō* jointly edited by Kazuhiro Nagata and Hiroshi Handa (publisher: Springer Verlag Tokyo), etc.

Figure 10A:
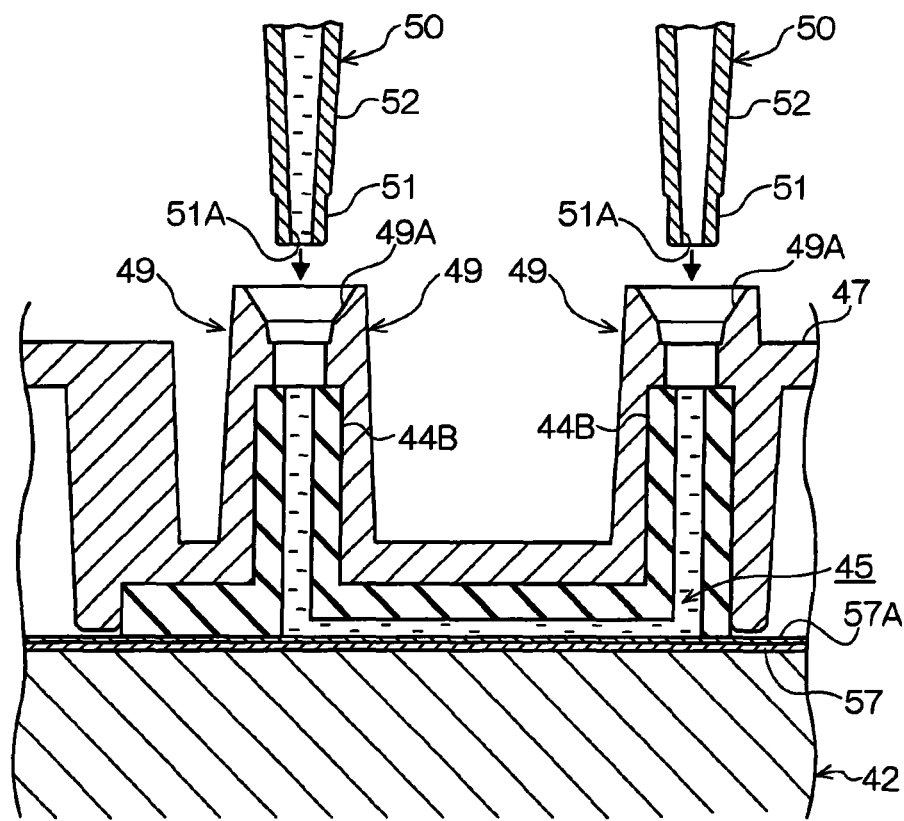
FIG. 10A is a view showing a state before the pipette tips are inserted into one receiving portion pertaining to the exemplary embodiment of the invention.
Figure 10B:
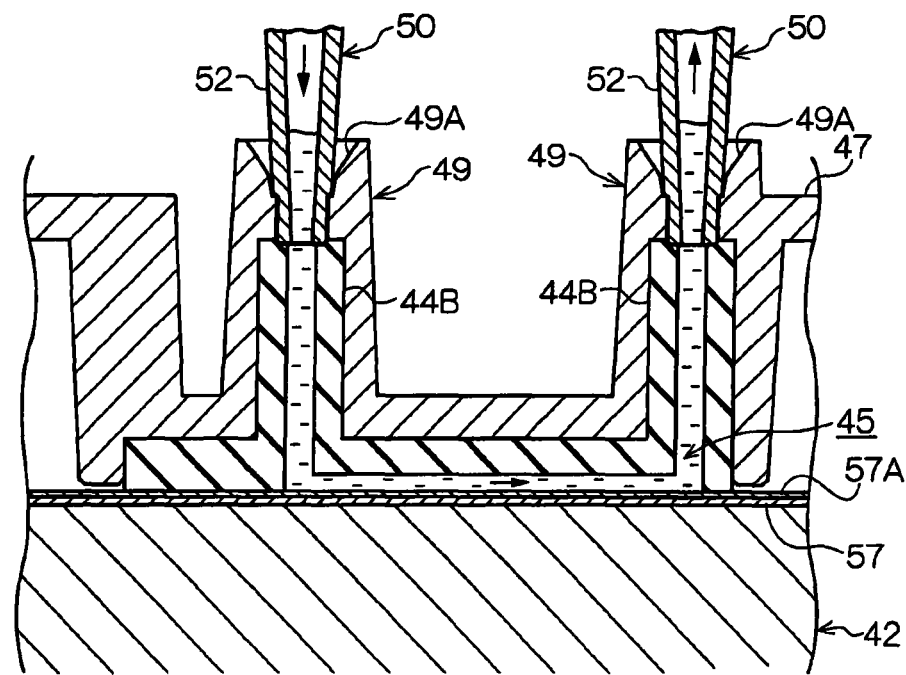
FIG. 10B is a view showing a state where the pipette tips have been inserted into one receiving portion pertaining to the exemplary embodiment of the invention.

When the sensor stick 40 is disposed in the assay unit 56, irradiation with the light beams L1 and L2 is performed, and output of the total reflection angle data begins, then the analyte solution YA stored in the analyte solution plate 17 is drawn into one of the pipette tips 50 attached to the head 24. Then, the pipette tip 50 is moved over the sensor stick 40 as shown in FIG. 10A and inserted into the recessed portion 49A of the receiving portion 49 as shown in FIG. 10B.

At this time, because the upper inner wall portion 49F configuring the uppermost portion of the recessed portion 49A and the central inner wall portion 49E have tapered shapes, the pipette tip 50 can be smoothly guided into the center from the distal end portion 51 side as shown in FIG. 11A even if the insertion position of the pipette tip 50 is shifted somewhat. Further, because the inner peripheral step portion 49D also has a tapered shape, shock resulting from contact between the distal end portion 51 and the inner peripheral step portion 49D can be reduced as shown in FIG. 11B, and the distal end portion 51 can be smoothly inserted toward the flow path member 44.

When the pipette tip 50 is inserted into the recessed portion 49A and pushed toward the flow path member 44, as shown in FIG. 11C, the upper end portion of the circular cylinder member 44B configured by a soft material becomes deformed, the distal end portion 51 of the pipette tip 50 eats into the upper end portion of the circular cylinder member 44B, and the outer peripheral step portion 52A and the inner peripheral step portion 49D contact each other. Further, the first inner wall portion 49E has a shape along the distal end portion 51 of the pipette tip 50, and the opening 51A in the pipette tip 50 is disposed at a position where it communicates with the exit/entry opening 43 of the liquid flow path 45. In this manner, positioning in the vertical direction and the surface direction between the opening 51A in the pipette tip 50 and the exit/entry opening 43 of the liquid flow path 45 is performed, and a communication path for dispensing and drawing in liquid such as the analyte solution YA is configured between the inner portion of the pipette tip 50 and the liquid flow path 45. In this state, as shown in FIG. 10B, the analyte solution YA is dispensed from one pipette tip 50 and the buffer liquid inside the liquid flow path 45 is drawn in by the other pipette tip 50, whereby the analyte solution YA can be supplied to the liquid flow path 45.

In the present exemplary embodiment, as mentioned previously, positioning is performed not by inserting the pipette tip 50 inside the liquid flow path 45 but by inserting the distal end portion 51 inside the first inner wall portion 49E and causing the inner peripheral step portion 49D and the outer peripheral step portion 52A to contact each other, and supply of liquid is performed by disposing the opening 51A in the pipette tip 50 in the exit/entry opening 43 of the liquid flow path 45. Consequently, degradation of the distal end portion 51 resulting from pullout that occurs when the pipette tip 50 is inserted into the liquid flow path 45 to supply liquid is controlled.

Further, because the pipette tip 50 is not inserted into the liquid flow path 45, the injection amount can be stabilized without the liquid flow path 45 being pushed apart, and the height of the surface of the liquid after the pipette tip 50 has been pulled out can be made constant.

Further, because the liquid flow path member 44 is configured by a soft material and is pushed apart and deformed by the distal end portion 51 of the pipette tip 50, the pipette tip 50 and the receiving portion 49 can be tightly adhered together.

It will be noted that, although in the present exemplary embodiment an example was described where the liquid flow path 44 was configured by a soft material and the pipette tip 50 was configured by a material that was harder than that, the liquid flow path 44 may be configured by a hard material and the pipette tip 50 may be configured by a soft material such that the pipette tip 50 becomes deformed.

Further, because the pipette tip 50 is not inserted into the liquid flow path 45, a situation where the pipette tip 50 remains inserted in the liquid flow path 45 and ends up coming off of the nozzles 24B can also be prevented.

It will also be noted that, although in the present exemplary embodiment an example was described where the liquid supply device of the present invention was applied to a biosensor, the liquid supply device of the present invention can also be applied to other devices and particularly all kinds of devices that use pipette tips to supply small quantities of liquids to flow paths.

What is claimed is:

1. A liquid supply device into which liquid enters and from which liquid exits, comprising:
    a tapered pipette tip having a substantially circular cross-section and including a distal end portion, a body portion and an outer peripheral step portion disposed between the distal end portion and the body portion, the distal end portion having an opening therein that dispenses or draws in liquid, the diameter of the body portion being larger than the diameter of the distal end portion;
    a flow path member including an end surface having formed therein an exit/entry opening through which the liquid enters and from which the liquid exits and which defines a flow path communicated with the exit/entry opening, at least one of a surface of the distal end portion of the pipette tip and the end surface of the flow path member being elastically deformable; and
    a receiving member that at least partially circumscribes the flow path member and
includes a recessed portion that communicates with the exit/entry opening,
    wherein:
    the recessed portion is defined by:
        a first inner wall portion that has a length in an insertion direction of the pipette
    tip that is shorter than the length of the distal end portion in the insertion direction of the
    pipette tip, and
        a second inner wall portion having inner diameter that is larger than an inner
    diameter of the first inner wall portion and which includes an inner peripheral step portion adjacent the first inner wall portion, wherein the first inner wall portion is disposed closer to the flow path member than is the second inner wall portion, and a distal end surface of the pipette tip is pushed against an end surface of the flow path member in which the exit/entry opening is formed, whereby the opening in the pipette tip and the exit/entry opening of the flow path member are communicated with each other and the elastically deformable end surface of the pipette tip or the flow path member is deformed such that the outer peripheral step portion is brought into contact with the inner peripheral step portion.

2. The liquid supply device of claim 1, wherein the flow path member is formed of a material that is softer than a material of the pipette tip.

3. The liquid supply device of claim 1, wherein the flow path member is constructed of an elastically deformable material that is elastically deformed when the pipette tip is pushed against the flow path member.

4. The liquid supply device of claim 1, wherein the outer peripheral step portion is tapered, and the inner peripheral step portion of the receiving member has a tapered shape complimentary to the outer peripheral step portion.

5. The liquid supply device of claim 2, wherein the outer peripheral step portion is tapered, and the inner peripheral step portion of the receiving member has a tapered shape complimentary to the outer peripheral step portion.

6. The liquid supply device of claim 3, wherein the outer peripheral step portion is tapered, and the inner peripheral step portion of the receiving member has a tapered shape complimentary to the outer peripheral step portion.

* * * * *